(12) United States Patent
Sato

(10) Patent No.: US 8,415,636 B2
(45) Date of Patent: Apr. 9, 2013

(54) METHOD FOR INSPECTING TWO-DIMENSIONAL ARRAY X-RAY DETECTOR

(75) Inventor: Kenji Sato, Otsu Shiga (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/580,318

(22) PCT Filed: Mar. 3, 2011

(86) PCT No.: PCT/JP2011/054848
§ 371 (c)(1),
(2), (4) Date: Aug. 21, 2012

(87) PCT Pub. No.: WO2011/111590
PCT Pub. Date: Sep. 15, 2011

(65) Prior Publication Data
US 2012/0318999 A1  Dec. 20, 2012

(30) Foreign Application Priority Data

Mar. 9, 2010  (JP) .................................. 2010-051521

(51) Int. Cl.
*G01T 1/20* (2006.01)
(52) U.S. Cl. ................ 250/370.09; 250/252.1; 378/98.8
(58) Field of Classification Search ............... 250/252.1, 250/370.01, 370.08, 370.09; 348/246; 378/62, 378/98.8, 207
See application file for complete search history.

(56) References Cited

U.S. PATENT DOCUMENTS

| 6,512,217 B1 | 1/2003 | Kameshima |
| 2004/0252874 A1 | 12/2004 | Yamazaki |
| 2006/0208195 A1 | 9/2006 | Petrick et al. |

FOREIGN PATENT DOCUMENTS

| JP | 2000-046646 A | 2/2000 |
| JP | 2005-006196 A | 1/2005 |
| JP | 2006-267101 A | 10/2006 |
| JP | 2008-301883 A | 12/2008 |
| JP | 2008-305959 A | 12/2008 |

OTHER PUBLICATIONS

International Search Report issued in PCT/JP2011/054848 issued on Jun. 7, 2011.

*Primary Examiner* — Mark R Gaworecki
(74) *Attorney, Agent, or Firm* — McDermott Will & Emery LLP

(57) ABSTRACT

Disclosed is a two-dimensional X-ray detector array inspection method capable of recognizing two-dimensional X-ray detector arrays unsuitable for X-ray imaging by means of identifying quickly growing defective pixels. The two-dimensional X-ray detector array inspection method involves a bias voltage step for repeated supply and stopping of a bias voltage from a common electrode; a dark current value measurement step for measuring the pixel values of pixels in a non-X-ray-irradiating state; a defective pixel identification step for identifying defective pixels on the basis of the pixel values of the pixels measured in the dark current value measurement step; and a determination step for determining whether or not the two-dimensional X-ray array detector is suitable on the basis of the size of the missing pixel chunks or the total number of defective pixels identified in defective pixel identification step.

20 Claims, 10 Drawing Sheets

(a)

(b)

(a)

(b)

METHOD FOR INSPECTING TWO-DIMENSIONAL ARRAY X-RAY DETECTOR

RELATED APPLICTION

This appliction is the U.S. National Phase under U.S.C. §371 of International Application No. PCT/JP2011/054848 filed on Mar. 3, 2011, which claims the benefit of Japanese Application No. 2010-051521, filed Mar. 9, 2010, the disclosures of which Applications are incorporated by reference herein.

TECHNICAL FIELD

The present invention relates to a method for inspecting a two-dimensional array X-ray detector.

BACKGROUND ART

As a two-dimensional array X-ray detector that is used for an X-ray imaging apparatus, for example, a flat panel detector (FPD) is known. The flat panel detector has a configuration in which, on a substrate on which switching elements such as TFTs are arranged in a two-dimensional array (matrix), a converting film made of a-Se (amorphous selenium) or the like is evaporated. In the flat panel detector, when an image of X-rays passing through a test object is projected onto the converting film, charge signals proportional to shading of the image are generated in the converting film. The charge signals are collected by pixel electrodes that are arranged in a two-dimensional array and accumulated in electrostatic capacitors (capacitors). Charges accumulated in the electrostatic capacitors are read as the switching elements are operated, and transmitted to an image processing part as electrical signals, where image processing is performed (see Patent literature 1).

CONVENTIONAL TECHNIQUE LITERATURE

Patent Literature

[Patent literature 1] JPA 2008-301883

SUMMARY OF THE INVENTION

Problem to be Solved by the Invention

In such a two-dimensional array X-ray detector using the converting film made of a-Se or the like, defective pixels may appear during a manufacturing process. During use of the two-dimensional array X-ray detector, part of such defective pixels rapidly grows in number and size to block X-ray imaging in a short period of time. In the two-dimensional X-ray detector in which defective pixels having growth potential resulting in the rapid growth in a short period of time as described are present, the defective pixels make correct X-ray imaging impossible, and therefore the two-dimensional X-ray detector cannot be used for an X-ray imaging apparatus or the like.

Meanwhile, it is not that all of the defective pixels are the defective pixels having the growth potential resulting in the rapid growth in a short period of time. Regarding defective pixels not having such growth potential, by making defect registrations to complement pixel values, the two-dimensional array X-ray detector provided with such defective pixels can be used for X-ray imaging.

For this reason, it is necessary to determine whether or not a defective pixel is one that rapidly grows or one of which a size does not change; however, even in consideration of the number, sizes, and the like of defects in the two-dimensional array X-ray detector, such determination cannot be made at present.

The present invention is made in order to solve the above-described problem, and an object thereof is to provide a method for inspecting a two-dimensional array X-ray detector, which can recognize a two-dimensional array X-ray detector unsuitable for X-ray imaging by identifying a defective pixel having growth potential resulting in growth of a size of the defective pixel in a short period of time.

Means Adapted to Solve the Problem

An invention according to a first aspect of the present invention is a method for inspecting a two-dimensional array X-ray detector that is provided with: a converting film that is sensitive to X-rays and outputs a charge signal corresponding to an incident X-ray amount; a common electrode that is formed on a surface of the converting film and supplies bias voltage to the converting film; a plurality of pixel electrodes that are arranged on a surface of the converting film in a matrix corresponding to the pixels, the surface being on a side opposite to the common electrode; a plurality of storage capacitors that are respectively connected to the pixel electrodes and store charge signals; switching elements that are respectively connected to the pixel electrodes; a gate driver that, upon reading of the signals, sequentially turns on the respective switching elements through gate bus lines; and a data collection part that reads the charge signals stored in the respective storage capacitors through data bus lines, the method being provided with: a bias voltage step of repeating supply of the bias voltage through the common electrode and a stop of the supply a plurality of times; a dark current value measuring step of measuring pixel values of the respective pixels in a state where X-rays are not irradiated; a defective pixel identifying step of identifying defective pixels on a basis of the pixel values of the respective pixels, the pixel values being measured in the dark current value measuring step; and a determination step of, on a basis of a total number of the defective pixels identified in the defective pixel identifying step or a size of a defective pixel block, determining whether or not the two-dimensional array X-ray detector is usable.

An invention according to a second aspect of the present invention is the invention according to the first aspect, wherein a time to supply the bias voltage and a time to stop the supply of the bias voltage in the bias voltage step are times that are, by measuring a change in the total number of the defective pixels or the size of the defective pixel block with time, preset as periods for a charge state of the converting film to stabilize.

An invention according to a third aspect of the present invention is a method for inspecting a two-dimensional array X-ray detector that is provided with: a converting film that is sensitive to X-rays and outputs a charge signal corresponding to an incident X-ray amount; a common electrode that is formed on a surface of the converting film and supplies bias voltage to the converting film; a plurality of pixel electrodes that are arranged on a surface of the converting film in a matrix corresponding to the pixels, the surface being on a side opposite to the common electrode; a plurality of storage capacitors that are respectively connected to the pixel electrodes and store charge signals; switching elements that are respectively connected to the pixel electrodes; a gate driver that, upon reading of the signals, sequentially turns on the respective switching elements through gate bus lines; and a data collection part that, through data bus lines, reads the charge signals stored in the respective storage capacitors, the method being provided with: a bias voltage step of repeating supply of the bias voltage and supply of reverse bias voltage through the common electrode a plurality of times; a dark current value measuring step of measuring pixel values of the respective pixels in a state where X-rays are not irradiated; a defective pixel identifying step of identifying defective pixels on a basis of the pixel values of the respective pixels, the pixel values being measured in the dark current value measuring step; and a determination step of, on a basis of a total number of the defective pixels identified in the defective pixel identifying step or a size of a defective pixel block, determining whether or not the two-dimensional array X-ray detector is usable.

An invention according to a fourth aspect of the present invention is the invention according to the third aspect, wherein a time to supply the bias voltage and a time to supply the reverse bias voltage in the bias voltage step are times that are, by measuring a change in the total number of the defective pixels or the size of the defective pixel block with time, preset as periods for a charge state of the converting film to stabilize.

An invention according to a fifth aspect of the present invention is the invention according to any of the first to fourth aspects, wherein in the determination step, on a basis of the defective pixels that are identified in the defective pixel identifying step, a defect map is created, and on a basis of the defect map, it is determined whether or not the two-dimensional array X-ray detector is usable.

An invention according to a sixth aspect of the present invention is the invention according to the fifth aspect, further provided with: an initial defect map creating step of, before the bias voltage step, creating an initial defect map, wherein in the determination step, the defect map that is created on the basis of the defective pixels identified in the defective pixel identifying step, and the initial defect map that is created in the initial defect map creating step are compared with each other to thereby determine whether or not the two-dimensional array X-ray detector is usable.

An invention according to a seventh aspect of the present invention is the invention according to any of the first to fourth aspects, wherein in the dark current value measuring step, in a state where the converting film is not irradiated with any X-ray, the switching elements are sequentially turned on to detect the charge signals of the respective pixels.

An invention according to an eighth aspect of the present invention is the invention according to any of the first to seventh aspects, wherein in the bias voltage step, the converting film is heated.

Effects of the Invention

According to the inventions according to the first and second aspects, by repeating the supply of the bias voltage and the stop of the supply through the common electrode the plurality of times to place stress on the converting film, the defective pixels can be prompted to grow. For this reason, defective pixels having growth potential resulting in growth of the number or sizes of them in a short period of time can be identified, and therefore a two-dimensional array X-ray detector unsuitable for X-ray imaging can be recognized.

According to the inventions according to the third and fourth aspects, by repeating the supply of the bias voltage and the supply of the reverse bias voltage through the common electrode the plurality of times to place stress on the converting film, the defective pixels can be prompted to grow in a short period of time. For this reason, defective pixels having the growth potential resulting in growth of the number or sizes of them in a short period of time can be identified, and therefore a two-dimensional array X-ray detector unsuitable for X-ray imaging can be recognized.

According to the invention according to the fifth aspect, on the basis of the defect map, the total number of the defective pixels or the size of the defective pixel block can be recognized, on the basis of which defective pixels having the growth potential resulting in growth of the number or sizes of them in a short period of time can be identified, and therefore a two-dimensional array X-ray detector unsuitable for X-ray imaging can be recognized.

According to the invention according to the sixth aspect, the determination is made by comparing the defect map created on the basis of the defective pixels identified in the defective pixel identifying step with the initial defect map created in the initial defect map creating step, and therefore defective pixels having the growth potential resulting in growth of sizes of them in a short period of time can be accurately detected with being distinguished from the other defective pixels.

According to the invention according to the seventh aspect, by sequentially turning on the switching elements in the state where the converting film is not irradiated with any X-ray and thereby detecting the charge signals of the respective pixels, the dark current values can be accurately measured.

According to the invention according to the eighth aspect, by heating the converting film in the bias voltage step, the time for the charge state of the converting film to stabilize can be shortened. For this reason, the bias voltage step can be completed in a short period of time.

EMBODIMENTS OF THE INVENTION

Figure 1:
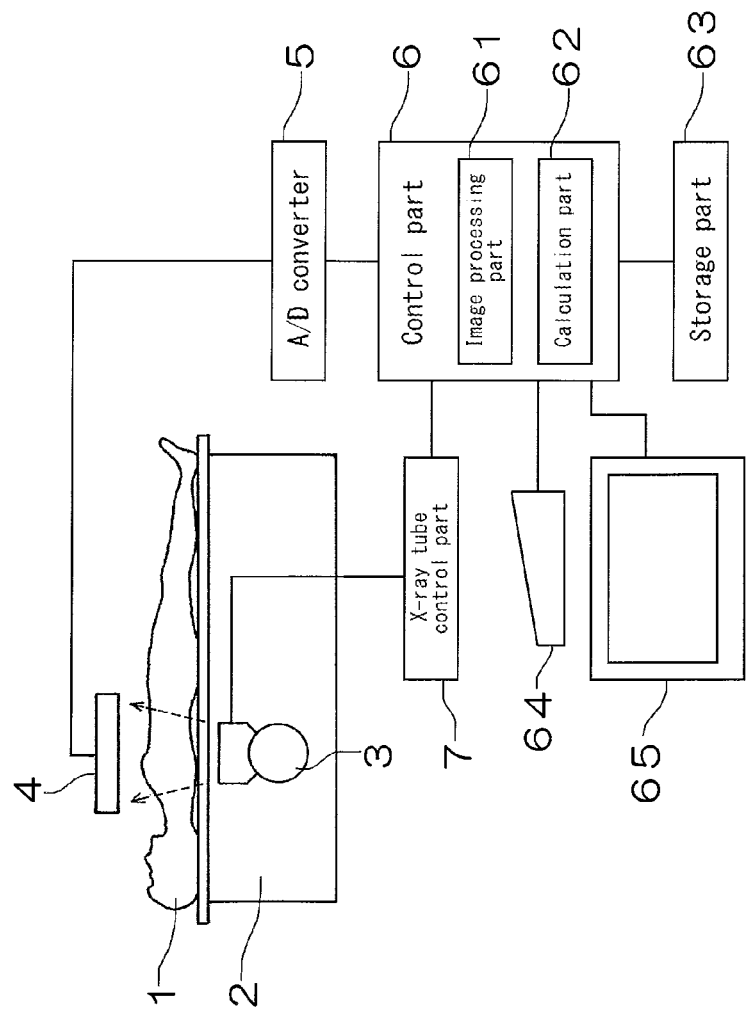
FIG. 1 is a schematic diagram of an X-ray imaging apparatus applied with the present invention.

Embodiments of the present invention will hereinafter be described with reference to the drawings. First, a configuration of an X-ray imaging apparatus applied with a flat panel detector 4 as a two-dimensional array X-ray detector according to the present invention is described. FIG. 1 is a schematic diagram of the X-ray imaging apparatus applied with the flat panel detector 4 according to the present invention.

The X-ray imaging apparatus is provided with: a table 2 for placing a test subject 1 serving as a test object; an X-ray tube 3; a flat panel detector 4; an A/D converter 5; a control part 6 that is provided with an image processing part 61 and a calculation part 62; a storage part 63; an input part 64 such as a keyboard; display part 65 such as a CRT; and an X-ray tube control part 7 that controls tube voltage or the like, which is to be supplied to the X-ray tube 3.

The X-ray imaging apparatus is configured to: irradiate X-rays from the X-ray tube 3 toward the test subject 1 on the table 2; detect X-rays passing through the test subject 1 with the flat panel detector 4; perform image processing of the detected X-rays in the image processing part 61; and use a video signal based on the image-processed X-rays to display an X-ray fluoroscopic image on the display part 65.

Figure 2:
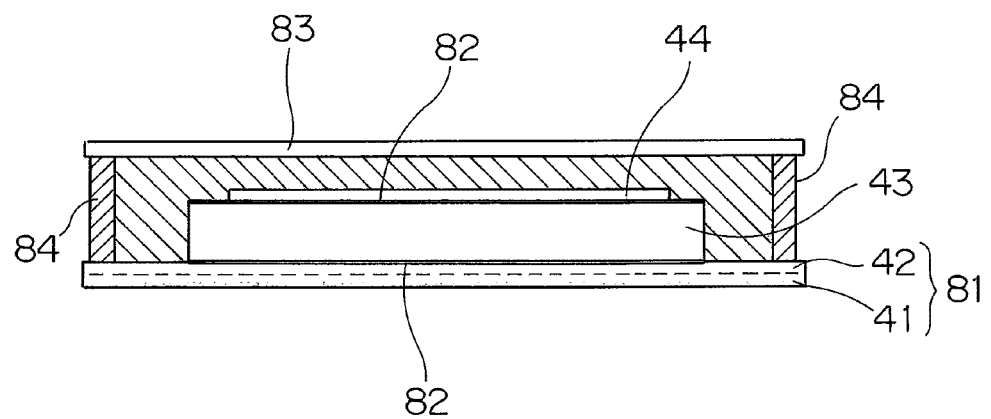
FIG. 2 is a schematic diagram of a flat panel detector 4.

Next, a configuration of the flat panel detector 4 is described. FIG. 2 is a schematic diagram of the flat panel detector 4.

As illustrated in FIG. 2, the flat panel detector 4 is provided with: a substrate 81 that is configured to have a glass substrate 41 and a TFT (thin film transistor) 42; a converting film 43 that is evaporated on the substrate 81 and made of a-Se or the like; and a common electrode 44 that is arranged on the converting film 43. On both surfaces of the converting film 43, carrier-selective high-resistance films 82 are formed. Also, the converting film 43 and common electrode 44 are surrounded by an insulating auxiliary plate 83 and a spacer 84, and in a space formed by the insulating auxiliary plate 83, spacer 84, and substrate 81, curable synthetic resin such as epoxy resin is filled.

Figure 3:
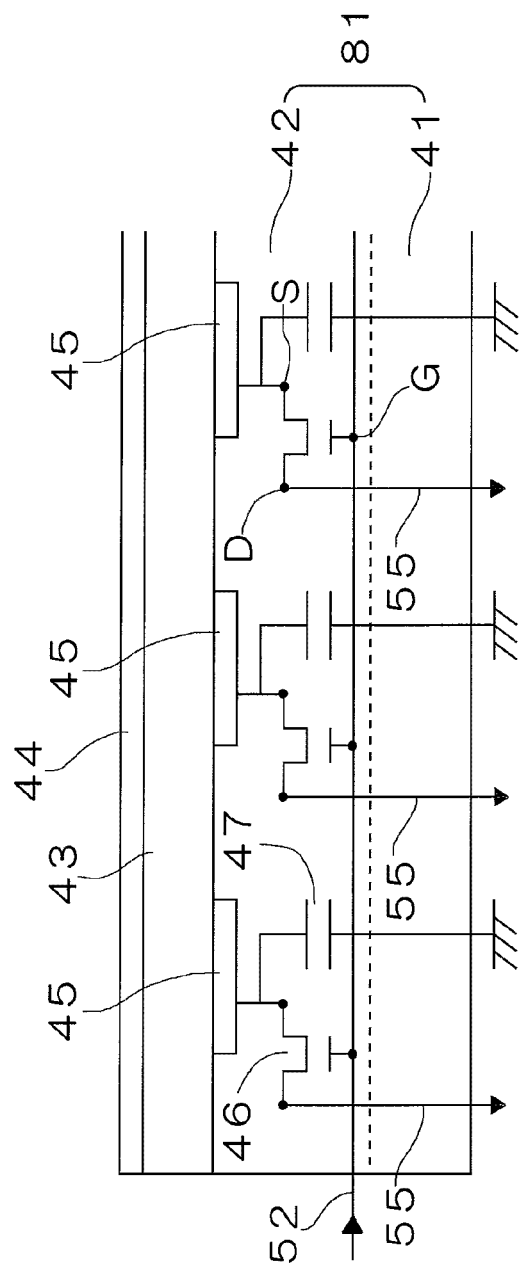
FIG. 3 is an equivalent circuit in a side view of the flat panel detector 4.
Figure 4:
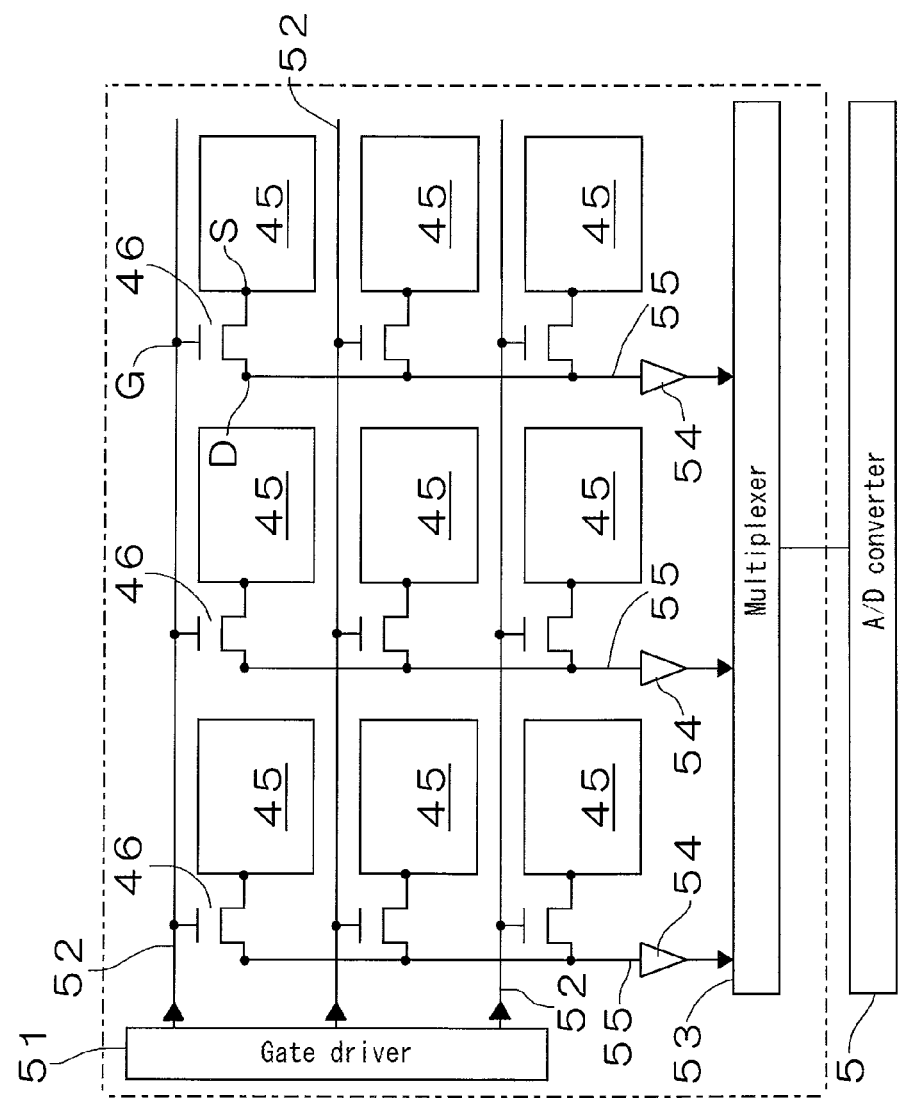
FIG. 4 is an equivalent circuit in a plan view of the flat panel detector 4.

FIG. 3 is an equivalent circuit in a side view of the flat panel detector 4. Also, FIG. 4 is an equivalent circuit in a plan view of the flat panel detector 4. Note that, in FIGS. 3 and 4, illustration of the carrier-selective high-resistance films 82 is omitted.

The flat panel detector 4 is, as described above, provided with: the glass substrate 41; TFT 42 that is formed on the glass substrate 41; converting film 43 that is evaporated on the TFT 42 and made of a-Se or the like; and common electrode 44 that is arranged on the converting film 43. In the TFT 42, pixel electrodes 45 serving as charge collecting electrodes are disposed in a horizontal and vertical matrix arrangement, i.e., a two-dimensional array arrangement. The pixel electrodes 45 are arranged, for example, in row and column directions, 1024 electrodes×1024 electrodes are arranged. FIGS. 3 and 4 schematically illustrate the case where 3 electrodes×3 electrodes are arranged in the row and column directions. Each of the pixel electrodes 45 is connected with a switching element 46 and an electrostatic capacitor (capacitor) 47.

Each of the pixel electrodes 45 is connected to a source S of a corresponding switching element 46. A gate driver 51 illustrated in FIG. 4 is connected with a plurality of gate bus lines 52, and the gate bus lines 52 are connected to gates G of the switching elements 46. On the other hand, as illustrated in FIG. 4, a multiplexer 53 that collects charge signals to output them as one signal is connected with a plurality of data bus lines 55 through amplifiers 54, and the data bus lines 55 are connected to drains D of the respective switching elements 46.

In the flat panel detector 4, when an image of X-rays that have passed through the test subject 1 is projected onto the converting film 43, charge signals (carriers) that are proportional to shading of the image are generated in the converting film 43. The charge signals are collected by the pixel electrodes 45 that are arranged in the two-dimensional array, and stored in the electrostatic capacitors 47. Then, by supplying voltage to the gate bus lines 52 from the gate driver 51 with bias voltage being supplied through the common electrode 44, the gates G of the respective switching elements 46 are brought into an on state. This causes the charge signals stored in the electrostatic capacitors 47 to be read to the data bus lines 55 through the sources S and drains D of the switching elements 46. The charge signals read to the respective data bus lines 55 are amplified by the amplifiers 54, and brought into one charge signal by the multiplexer 53, which is then outputted. The charge signal is digitalized by the A/D converter 5, and outputted as an X-ray detection signal to the control part 6 illustrated in FIG. 1.

In the flat panel detector 4 having such a configuration, due to properties of the converting film or carrier-selective high-resistance films 82, defective pixels may appear in a manufacturing process. Also, part of the defective pixels rapidly grows in size during use of the flat panel detector 4. In the present invention, by repeatedly supplying the bias voltage to the common electrode 44, it is determined whether or not a defect present in the flat panel detector 4 is a defect having such growth potential.

Figure 5:
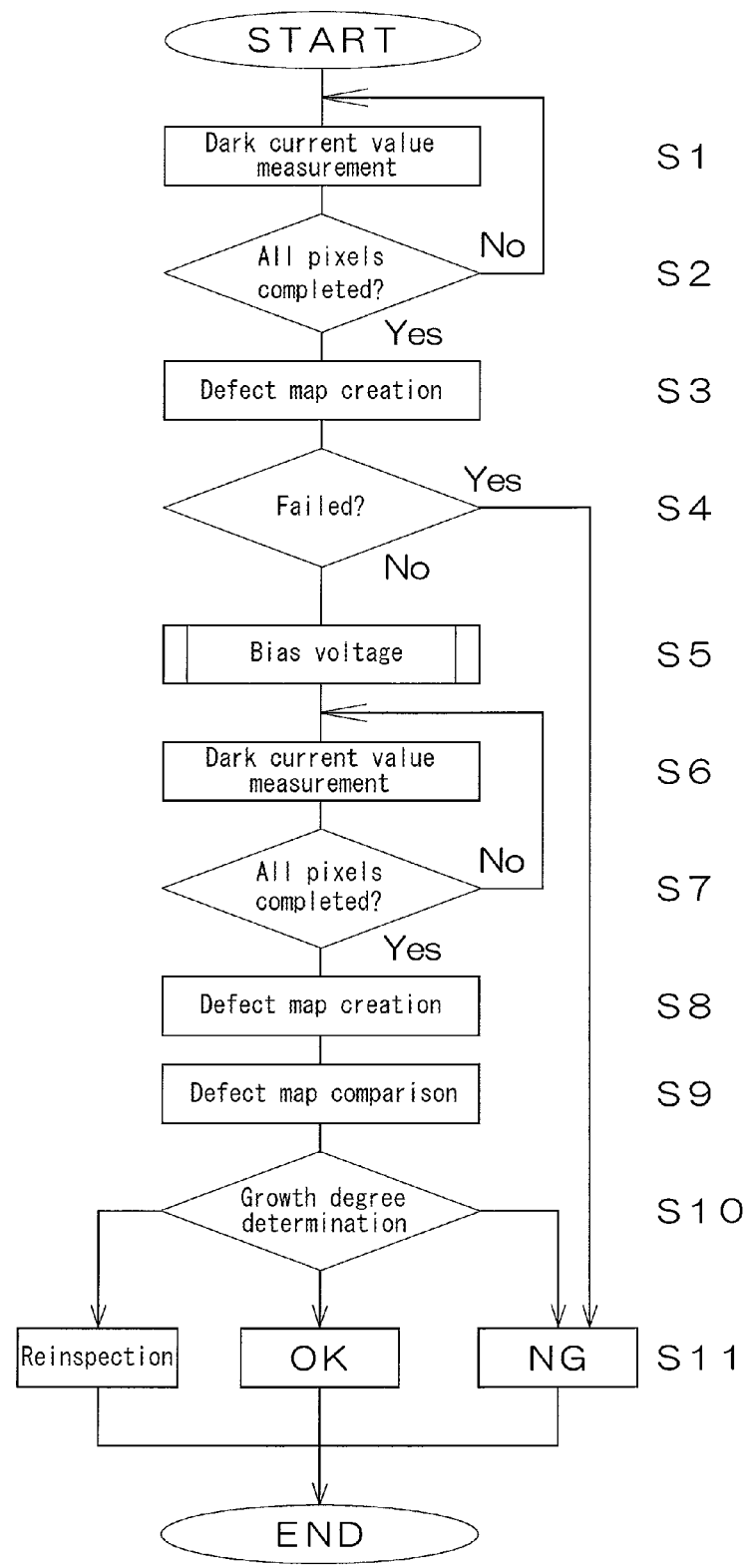
FIG. 5 is a flowchart illustrating a method for inspecting a two-dimensional array X-ray detector according to the present invention.

In the following, a method for inspecting a two-dimensional array X-ray detector according to the present invention is described. FIG. 5 is a flowchart illustrating the method for inspecting a two-dimensional array X-ray detector according to the present invention.

In the method for inspecting a two-dimensional array X-ray detector according to the present invention, first, a dark current value of each pixel is measured (Step S1). In this step, by sequentially turning on the switching elements 46 without irradiating the converting film 43 in the flat panel detector 4 with an X-ray, a charge signal of each pixel of the flat panel detector 4 is detected as a pixel value. The pixel value of each pixel at this time is stored as the dark current value. In addition, a pixel value of a normal pixel is also preliminarily stored.

If the measurement of the dark current value is completed for all pixels (Step S2), an initial defect map is created by, for each of the pixels in the flat panel detector 4, comparing the dark current value that is a pixel value of each of the pixels in the state where no X-ray is irradiated with the pixel value of a normal pixel (Step S3). In this case, for example, pixels each of which the dark current value is two or more times larger than the pixel value of a normal pixel are determined as defective pixels, and positions or the like of the defective pixels are mapped and stored as the initial defect map.

For example, the dark current value of a normal pixel of a typical flat panel detector 4 is approximately 2 pico amperes. For this reason, the determination of the defective pixel is based on whether or not the dark current value is equal to or more than 4 pico amperes.

In this step, if the number of the defective pixels exceeds a preset reference value, or a size of any of defective pixel blocks exceeds a preset reference value, the flat panel detector 4 is recognized as a defective product (Step S4), and then discarded or reused (Step S11).

Figure 6:
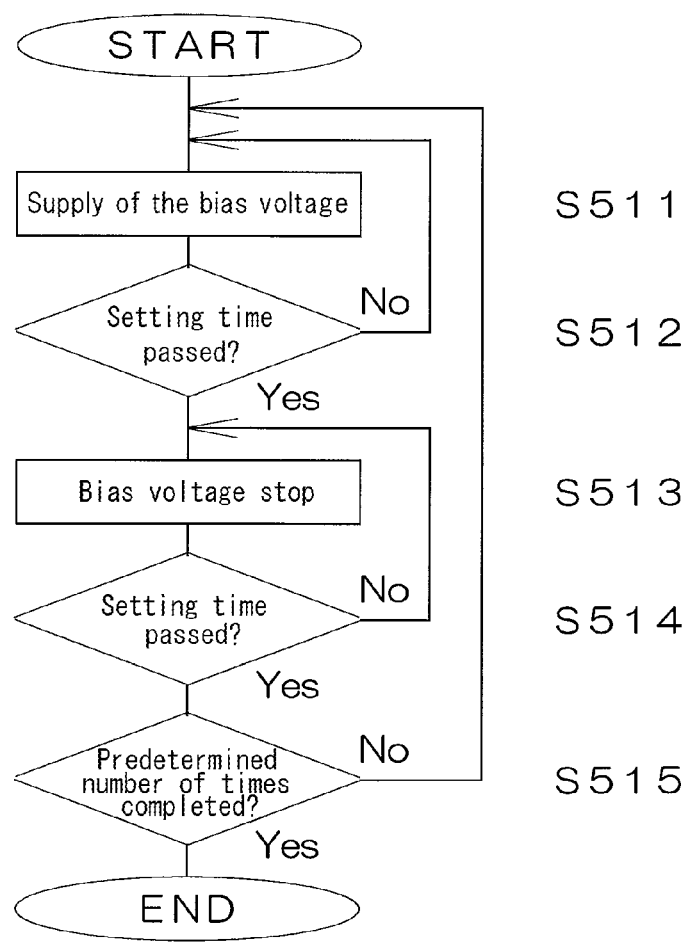
FIG. 6 is a flowchart illustrating a bias voltage step according to a first embodiment of the present invention.

Subsequently, a bias voltage step is performed (Step S5). The bias voltage step is performed according to a subroutine illustrated in FIG. 6. FIG. 6 is a flowchart illustrating the bias voltage step according to a first embodiment of the present invention.

In the bias voltage step, first, the bias voltage is supplied (Step S511). The supply of the bias voltage is performed through the common electrode 44 illustrated in FIGS. 2 and 3. If a supply time of the bias voltage has passed (Step S512), the supply of the bias voltage is stopped (Step S513). Then, the passage of a supply stop time of the bias voltage is waited (Step S514). The supply and supply stop of the bias voltage are repeated a preset number of times (Step S515).

Figure 7:
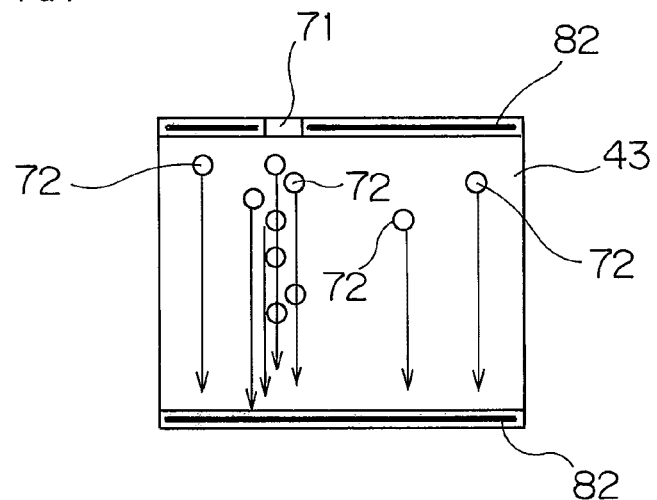
FIGS. 7 (a) and 7 (b) are schematic diagrams illustrating states of a converting film 43 at the times when bias voltage is supplied and stopped, respectively.
Figure 7:
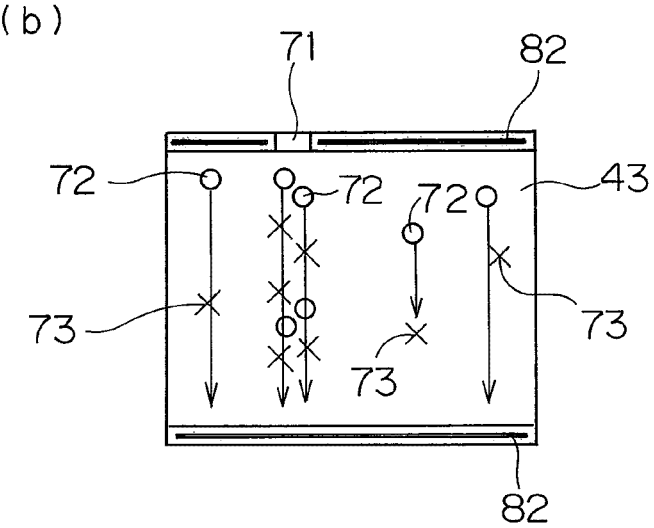

FIGS. 7 (a), 7 (b), 8 (a) and 8 (b) are schematic diagrams illustrating states of the converting film 43 at the times when the bias voltage is supplied and stopped, respectively. In addition, in these diagrams, reference numerals 71, 72, and 73 represent a defect, carrier (hole), and carrier trap, respectively.

Figure 8:
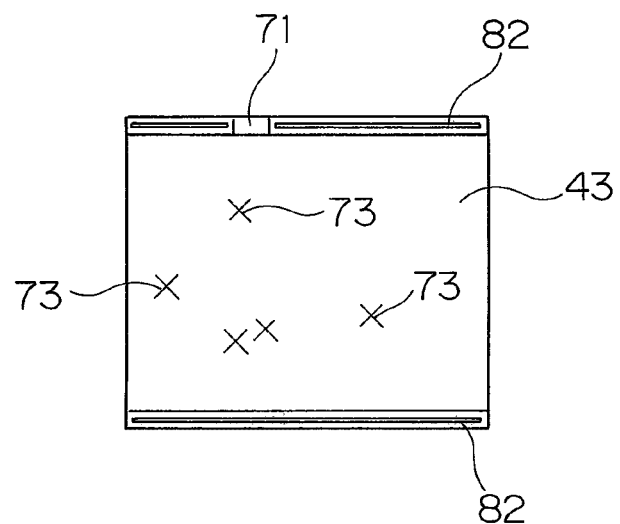
FIGS. 8 (a) and 8 (b) are schematic diagrams illustrating states of a converting film 43 at the times when bias voltage is supplied and stopped, respectively.
Figure 8:
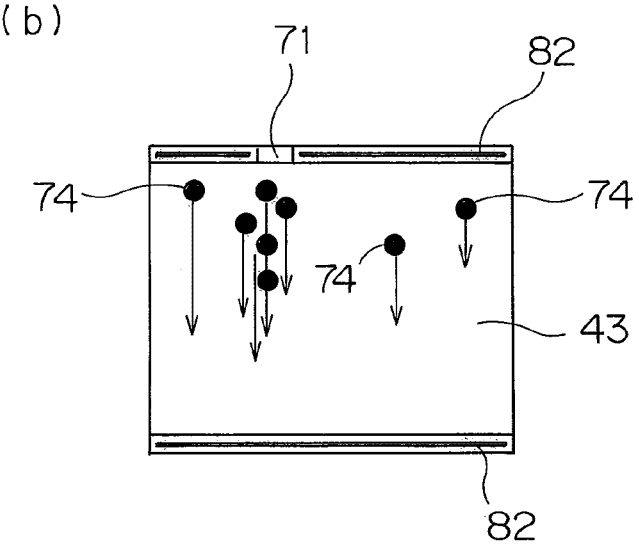

Immediately after the bias voltage is supplied, as illustrated in FIG. 7 (a), there is no carrier trap 73, and therefore a large amount of carrier current flows. However, as illustrated in FIG. 7 (b), the carrier traps 73 are gradually generated in the converting film 43 to limit the carrier current. If the supply of the bias current is stopped in this state, as illustrated in FIG. 8 (a), the carrier traps 73 are gradually eliminated. That is, a predetermined time is required for the carrier traps in the converting film 43 to emit the carriers 72.

During a period of a transient state from the supply of the bias voltage or the stop of the supply to stabilization of a charge state inside the converting film 43, high voltage is concentrated on an inhomogeneous part inside the converting film 43 or the carrier-selective high-resistance film layers 82, and heavier stress than that in a steady state is placed on the converting film 43. A region that is not resistant to the stress becomes the defective pixel where partial discharge occurs and dark current abnormally flows. If a current value of the dark current exceeds capacity of the electrostatic capacitor 47, charges overflow to surrounding pixels to give rise to the defective pixel block having a size corresponding to a few pixels.

As described above, if a constant time does not pass since the supply of the bias voltage or the stop of the supply, the charge state inside the converting film 43 does not stabilize, and therefore if the on/off period of the bias voltage is shorter than the period required for the charge state to stabilize, a test is not performed with the above-described stress being placed. For this reason, by preliminarily checking changes in the total number of defective pixels and sizes of defective pixel blocks of a typical flat panel detector 4, the time for the charge state in the converting film 43 to stabilize is obtained, and by making the on/off period of the bias voltage longer than the time, the occurrence of a defective pixel due to the stress can be accurately detected.

In order to determine the above-described on/off period of the bias voltage under the condition that, as the converting film 43, amorphous selenium was used, and as the carrier-selective high-resistance film layers 82, $Sb_2S_3$ (antimony sulfide) was used, a flat panel detector 4 in which three defective pixel blocks A, B, and C were present and the total number of the defective pixels was approximately 7000 out of 9 million pixels in total was used to make an experiment.

Table 1 below is a table that lists elapsed time and defect state after the start of the supply of the bias current. That is, the flat panel detector 4 that had not been supplied with the bias voltage for 7 days to sufficiently stabilize the charge state inside the converting film 43 was supplied with the same bias voltage as that at the time of normal use, and immediately after (1.5 minutes after), and at intervals of 60 minutes, such as after 60 minutes passed and after 120 minutes passed, changes in sizes of the defective pixel blocks and the number of defective pixels were directly measured. As is clear from Table 1 below, immediately after the supply of the bias voltage, there is no carrier trap, so that transient current flows and therefore the sizes of the defective pixel blocks and the number of defective pixels exhibit large values; however, after approximately 60 minutes has passed, the converting film 43 stabilizes. From this result, it turns out that, considering individual differences among respective flat panel detectors 4, it is appropriate to set the supply time of the bias voltage to approximately 90 minutes.

TABLE 1

| Elapsed time (minute) | Defect block A | Defect block B | Defect block C | Number of defects |
|---|---|---|---|---|
| 1.5 | 5 | 8 | 10 | 14734 |
| 60 | 5 | 6 | 6 | 6117 |
| 120 | 5 | 6 | 6 | 6257 |
| 180 | 5 | 5 | 6 | 6753 |
| 240 | 5 | 5 | 5 | 6903 |
| 300 | 4 | 5 | 5 | 7156 |
| 360 | 4 | 6 | 5 | 7500 |

Table 2 below is a table that lists elapsed time and defect state after the stop of the supply of the bias current. That is, the bias voltage supplied to the flat panel detector 4 that had been supplied with the bias voltage for 90 minutes or more to sufficiently stabilize the charge state inside the converting film 43 was stopped, and then at intervals of 10 minutes, changes in sizes of the defective pixel blocks and the number of defective pixels were measured. As is clear from Table 2 below, the sizes of the defective pixel blocks and the number of defective pixels are stabilized by the passage of approximately 60 minutes. From this result, it turns out that, considering the individual differences among the respective flat panel detectors 4, it is appropriate to set the supply stop time of the bias voltage to approximately 90 minutes.

TABLE 2

| Elapsed time (minute) | Defect block A | Defect block B | Defect block C | Number of defects |
|---|---|---|---|---|
| 10 | 5 | 8 | 10 | 10046 |
| 30 | 5 | 8 | 10 | 13913 |
| 60 | 5 | 10 | 10 | 14756 |
| 90 | 5 | 10 | 10 | 14161 |

Also, as a result of repeating the above-described supply of the bias voltage for 90 minutes and the supply stop of the bias voltage for 90 minutes and obtaining the number of repetition times required for the sizes of the defective pixel blocks and the number of defective pixels to stabilize, it turns out that, even considering the individual differences, by repeating this approximately 24 times, it can be checked whether or not the sizes of the defective pixel blocks and the number of defective pixels change.

Referring to FIG. 5 again, after the above-described bias voltage step has been completed, a dark current value of each of the pixels is again measured (Step S6). In this step as well, by sequentially turning on the switching elements 46 without irradiating the converting film 43 in the flat panel detector 4 with an X-ray, a charge signal of each of the pixels of the flat panel detector 4 is detected as a pixel value.

If the measurement of the dark current value is completed for all of the pixels (Step S7), a defect map is created by, for each of the pixels in the flat panel detector 4, comparing the dark current value that is a pixel value of each of the pixels in the state where no X-ray is irradiated with the pixel value of a normal pixel (Step S8). In this case as well, for example, pixels each of which the dark current is two or more times larger than the pixel value of a normal pixel are determined as the defective pixels, and positions or the like of the defective pixels are mapped and stored.

Then, by comparing the defect map with the initial defect map created in Step S3 (Step S9), growth degrees of the defective pixel blocks and a growth degree of the number of defective pixels are determined (Step S10). That is, it is determined as a corresponding growth degree whether or not a size of each of the defective pixel blocks grows or the total number of defective pixels grows.

If the growth degree is equal to or less than a constant, the flat panel detector 4 is determined as being suitable for use (Step S11). On the other hand, if the growth degree is equal to or more than the constant, the flat panel detector 4 is determined as being unsuitable for use, and therefore discarded or reused (Step S11). Further, if the growth degree takes the intermediate value, the flat panel detector 4 is reinspected (Step S11).

As described above, according to the method for inspecting a two-dimensional array X-ray detector according to the present invention, by repeating the supply and supply stop of the bias voltage through the common electrode 44 a plurality of times to thereby place the stress on the converting film 43, a defective pixel can be prompted to grow. For this reason, defective pixels having growth potential resulting in growth of sizes and number of the defective pixels in a short period of time can be identified, and therefore a flat panel detector 4 unsuitable for X-ray imaging can be recognized.

Figure 9:
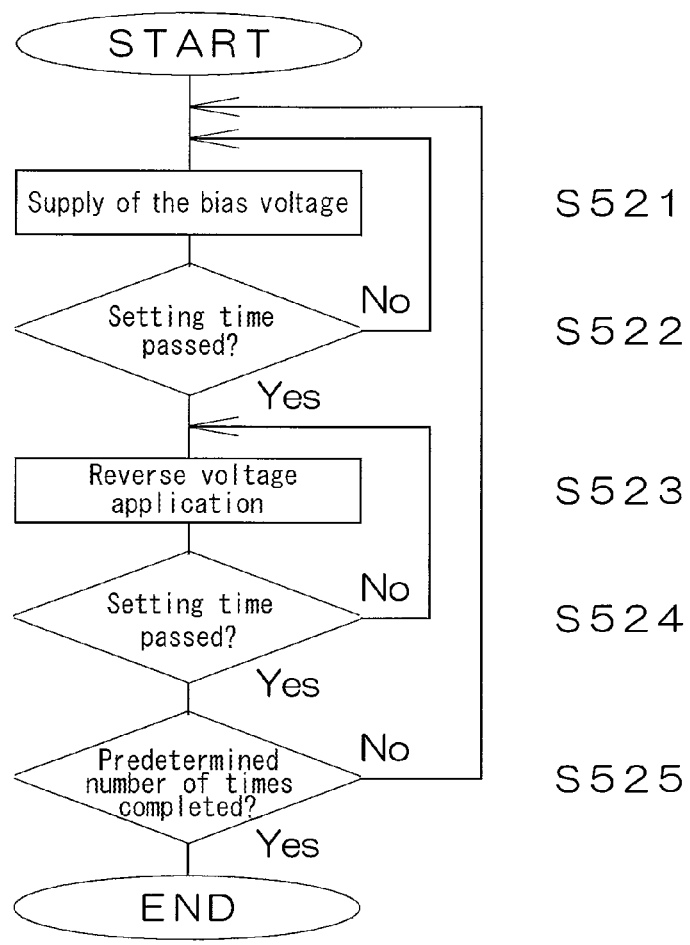
FIG. 9 is a flowchart illustrating a bias voltage step according to a second embodiment of the present invention.

Next, another embodiment of the present invention is described. FIG. 9 is a flowchart illustrating a bias voltage step according to a second embodiment of the present invention.

In the above-described bias voltage step according to the first embodiment, the supply and supply stop of the bias voltage are repeated a plurality of times. On the other hand, the bias voltage step according to the second embodiment is configured to repeat supply of bias voltage and supply of reverse bias voltage a plurality of times.

That is, as illustrated in FIG. 9, in the bias voltage step according to the second embodiment, first, as in the case of the first embodiment, the bias voltage is supplied (Step S521). The supply of the bias voltage is performed through the common electrode 44 illustrated in FIGS. 2 and 3. If a supply time of the bias voltage has passed (Step S522), the reverse bias voltage is then supplied (Step S523). The supply of the reverse voltage refers to, if the bias voltage is positive voltage, supply of negative voltage. The supply of the reverse bias voltage is performed through the common electrode 44 illustrated in FIGS. 2 and 3. Then, the passage of a supply time of the reverse bias voltage is waited (Step S524). The supply of the bias voltage and the supply of the reverse bias voltage are repeated a preset number of times (Step S525).

In the bias voltage step according to the second embodiment as well, immediately after the supply of the bias voltage, as illustrated in FIG. 7 (*a*), there is no carrier trap 73, and therefore a large amount of carrier current flows. However, as illustrated in FIG. 7 (*b*), the carrier traps 73 are gradually generated in the converting film 43 to limit the carrier current. If the reverse bias voltage is supplied in this state, as illustrated in FIG. 8 (*b*), the carriers 72 are forcibly injected, and thereby the carrier traps 73 are neutralized and eliminated immediately.

Table 3 below is a table that lists elapsed time and defect state after the supply of the reverse bias voltage. That is, as is clear from Table 2 below, sizes of defective pixel blocks and the number of defective pixels are stabilized by the passage of approximately 10 minutes since the supply of the reverse bias voltage. From this result, it turns out that, considering individual differences among respective flat panel detectors 4, it is appropriate to set the supply time of the reverse bias voltage to approximately 15 minutes.

TABLE 3

| Elapsed time (minute) | Defect block A | Defect block B | Defect block C | Number of defects |
|---|---|---|---|---|
| Reverse 10 | 5 | 10 | 10 | 13565 |

As described above, according to a method for inspecting a two-dimensional array X-ray detector according to the second embodiment of the present invention, by repeating the supply of the bias voltage and the supply of the reverse bias voltage through the common electrode 44 a plurality of times to thereby place stress on the converting film 43, a defective pixel can be prompted to grow. For this reason, defective pixels having growth potential resulting in growth of sizes and number of the defective pixels in a short period of time can be identified, and therefore a flat panel detector 4 unsuitable for X-ray imaging can be recognized. At this time, the supply of the reverse bias voltage enables a time required for the charge state in the flat panel detector 4 to stabilize can be shortened, and therefore a time required for the inspection can be shortened.

In addition, as the bias voltage at this time, for example, bias voltage at the time of normal use of the flat panel detector 4 can be set, and as the reverse bias voltage, an absolute value of it can be set to be equivalent to or smaller than the bias voltage. For example, the bias voltage may be set to +10000 volts, and the reverse bias voltage may be set to −5000 volts.

Figure 10:
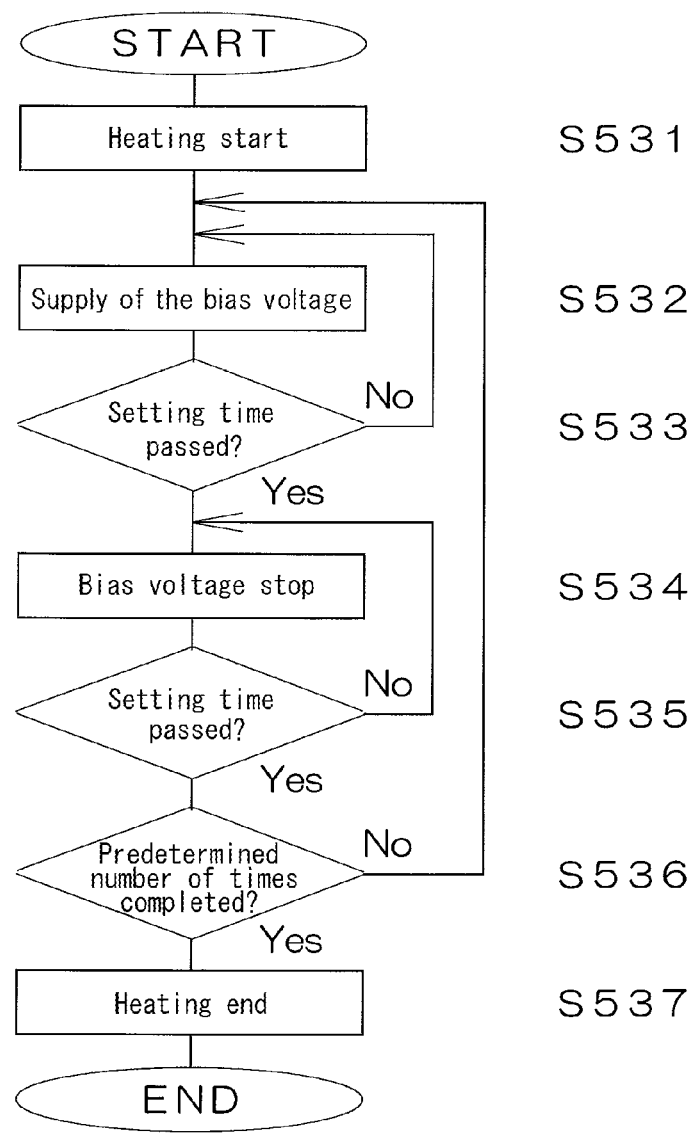
FIG. 10 is a flowchart illustrating a bias voltage step according to a third embodiment of the present invention.

Next, still another embodiment of the present invention is described. FIG. 10 is a flowchart illustrating a bias voltage step according to a third embodiment of the present invention.

The bias voltage step according to the third embodiment is configured to, while the supply and supply stop of the bias voltage in the bias voltage step according to the first embodiment are repeated the plurality of times, heat the converting film 43 and the like in the flat panel detector 4.

That is, in the bias voltage step according to the third embodiment, first, the flat panel detector 4 is heated (Step S531). After that, bias voltage is supplied (Step S532). Then, if a supply time of the bias voltage has passed (Step S533), the supply of the bias voltage is stopped (Step S534). Then, the passage of a supply stop time of the bias voltage is waited (Step S535). The supply and supply stop of the bias voltage are repeated a preset number of times (Step S536). After the supply and supply stop of the bias voltage have been completed the preset number of times, the heating of the flat panel detector 4 is stopped.

It is generally known that an emission time of the carrier 72 in the carrier trap 73 of the converting film 43 depends on temperature, and as the temperature is increased, the emission time of the carrier 72 becomes a short time. For this reason, by heating the converting film 43, such as raising temperature of an inspection environment of the flat panel detector 4, a time required for the charge state in the flat panel detector 4 to stabilize can be shortened, and therefore a time required for the inspection can be shortened.

In addition, in the third embodiment, while the supply and supply stop of the bias voltage are repeated the plurality of times as in the first embodiment, the converting film 43 is heated; however, the present invention may be adapted to heat the converting film 43 while the supply of the bias voltage and the supply of the reverse bias voltage are repeated the plurality of times as in the second embodiment.

In any of the above-described embodiments, a dark current value that serves as a reference for comparison at the time of determining a defective pixel is, with the dark current value of a normal pixel being used as a reference, preliminarily inputted and stored in the storage part 63 by an operator using the input part 64. However, an average value of dark current values of all pixels of the flat panel detector 4 may be set as the dark current value of a normal pixel.

Also, in any of the above-described embodiments, described is the case where the present invention is applied to the flat panel detector 4 used for the X-ray imaging apparatus; however, the present invention can also be applied to another two-dimensional array X-ray detector provided with a converting film that is sensitive to X-rays.

| [Explanations of letters or numerals] | |
|---|---|
| 1: | Test subject |
| 2: | Table |
| 3: | X-ray tube |
| 4: | Flat panel detector |
| 6: | Control part |
| 7: | X-ray tube control part |
| 41: | Glass substrate |
| 42: | TFT |
| 43: | Converting film |
| 44: | Common electrode |
| 45: | Pixel electrode |
| 46: | Switching element |
| 47: | Electrostatic capacitor |
| 51: | Gate driver |
| 52: | Gate bus line |
| 53: | Multiplexer |
| 54: | Amplifier |
| 55: | Data bus line |
| 61: | Image processing part |
| 62: | Calculation part |
| 63: | Storage part |
| 64: | Input part |
| 65: | Display part |
| 71: | Defect |
| 72: | Carrier |
| 73: | Carrier trap |
| 82: | Carrier-selective high-resistance film |

What is claimed is:

1. A method for inspecting a two-dimensional array X-ray detector that comprises:
    a converting film that is sensitive to X-rays and outputs a charge signal corresponding to an incident X-ray amount;
    a common electrode that is formed on a surface of the converting film and supplies bias voltage to the converting film;
    a plurality of pixel electrodes that are arranged on a surface of the converting film in a matrix corresponding to the pixels, the surface being on a side opposite to the common electrode;
    a plurality of storage capacitors that are respectively connected to the pixel electrodes and store charge signals;
    switching elements that are respectively connected to the pixel electrodes;
    a gate driver that, upon reading of the signals, sequentially turns on the respective switching elements through gate bus lines; and
    a data collection part that reads the charge signals stored in the respective storage capacitors through data bus lines, the method comprising:
    a bias voltage step of repeating supply of the bias voltage through the common electrode and a stop of the supply a plurality of times;
    a dark current value measuring step of measuring pixel values of the respective pixels in a state where X-rays are not irradiated;
    a defective pixel identifying step of identifying defective pixels on a basis of the pixel values of the respective pixels, the pixel values being measured in the dark current value measuring step; and
    a determination step of, on a basis of a total number of the defective pixels identified in the defective pixel identifying step or a size of a defective pixel block, determining whether or not the two-dimensional array X-ray detector is usable.

2. The method for inspecting a two-dimensional array X-ray detector, according to claim 1, wherein
    a time to supply the bias voltage and a time to stop the supply of the bias voltage in the bias voltage step are times that are, by measuring a change in the total number of the defective pixels or the size of the defective pixel block with time, preset as periods for a charge state of the converting film to stabilize.

3. The method for inspecting a two-dimensional array X-ray detector, according to claim 2, wherein
    in the determination step, on a basis of the defective pixels that are identified in the defective pixel identifying step, a defect map is created, and on a basis of the defect map, it is determined whether or not the two-dimensional array X-ray detector is usable.

4. The method for inspecting a two-dimensional array X-ray detector, according to claim 3, the method further comprising:
    an initial defect map creating step of, before the bias voltage step, creating an initial defect map, wherein
    in the determination step, the defect map that is created on the basis of the defective pixels identified in the defective pixel identifying step, and the initial defect map that is created in the initial defect map creating step are compared with each other to thereby determine whether or not the two-dimensional array X-ray detector is usable.

5. The method for inspecting a two-dimensional array X-ray detector, according to claim 2, wherein
    in the dark current value measuring step, in a state where the converting film is not irradiated with any X-ray, the switching elements are sequentially turned on to detect the charge signals of the respective pixels.

6. The method for inspecting a two-dimensional array X-ray detector, according to claim 2, wherein
    in the bias voltage step, the converting film is heated.

7. The method for inspecting a two-dimensional array X-ray detector, according to claim 1, wherein
    in the determination step, on a basis of the defective pixels that are identified in the defective pixel identifying step, a defect map is created, and on a basis of the defect map, it is determined whether or not the two-dimensional array X-ray detector is usable.

8. The method for inspecting a two-dimensional array X-ray detector, according to claim 7, the method further comprising:
    an initial defect map creating step of, before the bias voltage step, creating an initial defect map, wherein
    in the determination step, the defect map that is created on the basis of the defective pixels identified in the defective pixel identifying step, and the initial defect map that is created in the initial defect map creating step are compared with each other to thereby determine whether or not the two-dimensional array X-ray detector is usable.

9. The method for inspecting a two-dimensional array X-ray detector, according to claim 1, wherein in the dark current value measuring step, in a state where the converting film is not irradiated with any X-ray, the switching elements are sequentially turned on to detect the charge signals of the respective pixels.

10. The method for inspecting a two-dimensional array X-ray detector, according to claim 1, wherein
in the bias voltage step, the converting film is heated.

11. A method for inspecting a two-dimensional array X-ray detector that comprises:
a converting film that is sensitive to X-rays and outputs a charge signal corresponding to an incident X-ray amount;
a common electrode that is formed on a surface of the converting film and supply bias voltage to the converting film;
a plurality of pixel electrodes that are arranged on a surface of the converting film in a matrix corresponding to the pixels, the surface being on a side opposite to the common electrode;
a plurality of storage capacitors that are respectively connected to the pixel electrodes and store charge signals;
switching elements that are respectively connected to the pixel electrodes;
a gate driver that, upon reading of the signals, sequentially turns on the respective switching elements through gate bus lines; and
a data collection part that, through data bus lines, reads the charge signals stored in the respective storage capacitors, the method comprising:
a bias voltage step of repeating supply of the bias voltage and supply of reverse bias voltage through the common electrode a plurality of times;
a dark current value measuring step of measuring pixel values of the respective pixels in a state where X-rays are not irradiated;
a defective pixel identifying step of identifying defective pixels on a basis of the pixel values of the respective pixels, the pixel values being measured in the dark current value measuring step; and
a determination step of, on a basis of a total number of the defective pixels identified in the defective pixel identifying step or a size of a defective pixel block, determining whether or not the two-dimensional array X-ray detector is usable.

12. The method for inspecting a two-dimensional array X-ray detector, according to claim 11, wherein
a time to supply the bias voltage and a time to supply the reverse bias voltage in the bias voltage step are times that are, by measuring a change in the total number of the defective pixels or the size of the defective pixel block with time, preset as periods for a charge state of the converting film to stabilize.

13. The method for inspecting a two-dimensional array X-ray detector, according to claim 12, wherein
in the determination step, on a basis of the defective pixels that are identified in the defective pixel identifying step, a defect map is created, and on a basis of the defect map, it is determined whether or not the two-dimensional array X-ray detector is usable.

14. The method for inspecting a two-dimensional array X-ray detector, according to claim 13, the method further comprising:
an initial defect map creating step of, before the bias voltage step, creating an initial defect map, wherein
in the determination step, the defect map that is created on the basis of the defective pixels identified in the defective pixel identifying step, and the initial defect map that is created in the initial defect map creating step are compared with each other to thereby determine whether or not the two-dimensional array X-ray detector is usable.

15. The method for inspecting a two-dimensional array X-ray detector, according to claim 12, wherein
in the dark current value measuring step, in a state where the converting film is not irradiated with any X-ray, the switching elements are sequentially turned on to detect the charge signals of the respective pixels.

16. The method for inspecting a two-dimensional array X-ray detector, according to claim 12, wherein
in the bias voltage step, the converting film is heated.

17. The method for inspecting a two-dimensional array X-ray detector, according to claim 11, wherein
in the determination step, on a basis of the defective pixels that are identified in the defective pixel identifying step, a defect map is created, and on a basis of the defect map, it is determined whether or not the two-dimensional array X-ray detector is usable.

18. The method for inspecting a two-dimensional array X-ray detector, according to claim 17, the method further comprising:
an initial defect map creating step of, before the bias voltage step, creating an initial defect map, wherein
in the determination step, the defect map that is created on the basis of the defective pixels identified in the defective pixel identifying step, and the initial defect map that is created in the initial defect map creating step are compared with each other to thereby determine whether or not the two-dimensional array X-ray detector is usable.

19. The method for inspecting a two-dimensional array X-ray detector, according to claim 11, wherein
in the dark current value measuring step, in a state where the converting film is not irradiated with any X-ray, the switching elements are sequentially turned on to detect the charge signals of the respective pixels.

20. The method for inspecting a two-dimensional array X-ray detector, according to claim 11, wherein
in the bias voltage step, the converting film is heated.

* * * * *